(12) United States Patent
McGee

(10) Patent No.: US 9,067,944 B2
(45) Date of Patent: Jun. 30, 2015

(54) PROCESS FOR THE PREPARATION OF ANAGRELIDE AND ANALOGUES THEREOF

(75) Inventor: Paul McGee, Basingstoke (GB)

(73) Assignee: SHIRE LLC, Florence, KY (US)

( * ) Notice: Subject to any disclaimer, the term of this patent is extended or adjusted under 35 U.S.C. 154(b) by 0 days.

(21) Appl. No.: 13/878,651

(22) PCT Filed: Oct. 21, 2011

(86) PCT No.: PCT/GB2011/052053
§ 371 (c)(1),
(2), (4) Date: Apr. 10, 2013

(87) PCT Pub. No.: WO2012/052781
PCT Pub. Date: Apr. 26, 2012

(65) Prior Publication Data
US 2013/0211083 A1    Aug. 15, 2013

(30) Foreign Application Priority Data
Oct. 21, 2010    (GB) .................................. 1017783.0

(51) Int. Cl.
*C07D 487/04*    (2006.01)
*C07C 201/08*    (2006.01)
*C07C 227/18*    (2006.01)

(52) U.S. Cl.
CPC ............ *C07D 487/04* (2013.01); *C07C 201/08* (2013.01); *C07C 227/18* (2013.01)

(58) Field of Classification Search
CPC .................................................... C07D 487/04
See application file for complete search history.

(56) References Cited

U.S. PATENT DOCUMENTS

| 3,932,407 A | 1/1976 | Beverung, Jr. et al. |
| 4,146,718 A | 3/1979 | Jenks et al. |
| 4,208,521 A | 6/1980 | Crenshaw et al. |
| 4,357,330 A | 11/1982 | Fleming, Jr. et al. |
| RE31,617 E | 6/1984 | Beverung, Jr. et al. |
| 5,801,245 A | 9/1998 | Lang |

FOREIGN PATENT DOCUMENTS

| EP | 1373268 A2 | 1/2004 |
| EP | 1700840 A2 | 9/2006 |
| EP | 1700841 A2 | 9/2006 |
| EP | 1700842 A2 | 9/2006 |
| EP | 1700843 A2 | 9/2006 |
| EP | 1700859 A2 | 9/2006 |
| WO | WO 2004/033444 A1 | 4/2004 |
| WO | WO 2004/050657 A2 | 6/2004 |
| WO | WO 2009/138794 A1 | 11/2009 |
| WO | WO 2009/138796 A2 | 11/2009 |
| WO | WO 2010070318 A1 * | 6/2010 |

OTHER PUBLICATIONS

Goubko, C., et al. "Hydrogel cell patterning incorporating photocaged RGDS peptides." Biomed Microdevices. (2010), 12: pp. 555-568.*

* cited by examiner

*Primary Examiner* — Andrew D Kosar
*Assistant Examiner* — John S Kenyon
(74) *Attorney, Agent, or Firm* — Lucas & Mercanti, LLP

(57) ABSTRACT

The present invention relates to a novel process for producing anagrelide, 6,7-dichloro-1,5-dihydroimidazo[2,1-b]quinazolin 2(3H)-one, or certain analogs thereof. The process of the invention also provides improved processes for producing key intermediates required for the synthesis of anagrelide or certain analogs thereof.

11 Claims, No Drawings

PROCESS FOR THE PREPARATION OF ANAGRELIDE AND ANALOGUES THEREOF

CROSS REFERENCE TO RELATED APPLICATION

This application is a 371 of PCT/GB2011/052053, filed Oct. 21, 2011, which claims the benefit of GB Patent Application No. 1017783.0, filed Oct. 21, 2010, the contents of each of which are incorporated herein by reference.

FIELD THE INVENTION

This invention relates to a process for producing the 6,7-dichloro-1,5-dihydroimidazo[2,1-b]quinazolin 2 (3H)-one, more commonly known as anagrelide, and certain analogues thereof. More specifically, the present invention relates to an improved process for the formation of anagrelide and certain analogues thereof, which is efficient and viable to implement on a commercial scale.

BACKGROUND OF THE INVENTION

Anagrelide hydrochloride (AGRYLIN®, XAGRID®) is a novel orally administered imidazoquinazoline which selectively reduces platelet count in humans and is used for such purposes in the treatment of myeloproliferative diseases (MPDs), such as essential thrombocythemia (ET), where an elevated platelet count may put the patient at increased thrombotic risk. The chemical structure of anagrelide, 6,7-dichloro-1,5-dihydroimidazo[2,1-b]-quinazolin-2(3H)-one hydrochloride monohydrate, is shown as the hydrochloride monohydrate in the following formula:

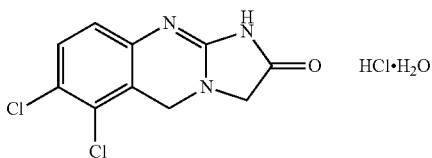

WO 2008/065444 discloses certain 3- and 5-substituted anagrelide derivatives that possess a more advantageous side effect profile. The 3- and 5-substituted anagrelide derivatives possess dramatically lower PDE III inhibitory activity when compared to anagrelide or its active metabolite, yet they still retain potent anti-megakaryocytic activity. The compounds described in WO 2008/065444 are therefore potentially useful and beneficial agents for the treatment of myeloproliferative diseases, such as essential thrombocythemia.

Processes for the preparation of anagrelide are described in U.S. Pat. Nos. 3,932,407; RE31,617; 4,146,718; 4,208,521; 4,357,330; and 5,801,245. Published European patent applications EP 1373268, EP 1700840, EP 1700841, EP 1700842, EP 1700843, and EP 170859 also describe methods for preparing anagrelide.

Commercially, as discussed in U.S. Pat. No. 5,801,245, and as shown in Scheme 1 below, anagrelide has been prepared as the hydrochloride monohydrate (compound IV) from the intermediate, ethyl-N-(6-amino-2,3-dichlorobenzyl)glycine (compound I), either by reaction with cyanogen bromide in hot alcoholic solution, or, preferentially, by reaction with cyanogen bromide in an aprotic solvent such as toluene to give the iminoquinazoline intermediate (compound II), which is isolated and then reacted with a base in a hot solution of alcohol to form anagrelide base (compound III).

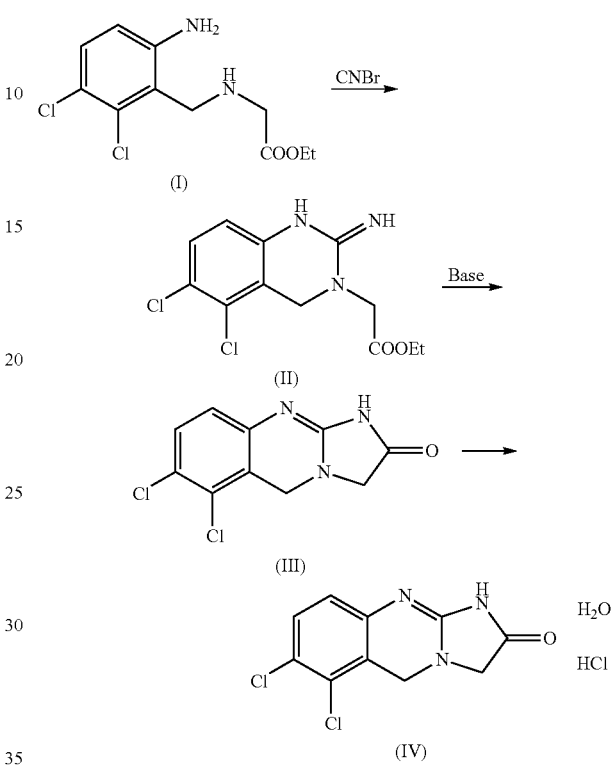

Scheme 1

The hydrochloride monohydrate anagrelide salt (compound IV) is prepared by adding hydrochloric acid to a methanol slurry of anagrelide base (compound III) and heating to reflux. The hydrochloride salt is then hydrated in a high humidity chamber. These two steps are time-consuming however, and the yield of hydrochloride salt can be poor due to competing acid hydrolysis of the lactam ring and methyl ester formation. After 15 minutes at reflux, the isolated yield is 62% and this decreases to 40% after 2 hours.

Normally, salts are prepared when the free base has undesirable properties such as poor solubility or a non-solid physical state. In this case, both anagrelide base (compound III) and the hydrochloride salt (compound IV) are solids with low aqueous solubility. In addition, the water of crystallization can accelerate decomposition of the parent molecuie through hydrolysis of the lactam ring and this presents long-term stability problems for pharmaceutical anagrelide formulations.

Radiolabeled anagrelide base has been used in pharmacokinetic studies in humans and monkeys and results show complete absorption into blood plasma demonstrating that the base is bioavailable. The free base is converted into the hydrochloride salt in the stomach to enhance absorption. Both the salt and the base exhibit equivalent pharmacological effects, and there is no inherent advantage to using the hydrochloride monohydrate salt as the active pharmaceutical agent.

An important intermediate in these prior art syntheses of anagrelide is ethyl-N-(6-amino-2,3-dichlorobenzyl)glycine (compound I). Ethyl-N-(6-amino-2,3-dichlorobenzyl)glycine (compound I) has been prepared from 2,3-dichloro-6- nitrobenzylamine (compound V) as shown in Scheme 2. This material is no longer readily available commercially, however, as the precursor 2,3-dichloro-nitrobenzonitrile has extreme toxic and skin-irritant properties.

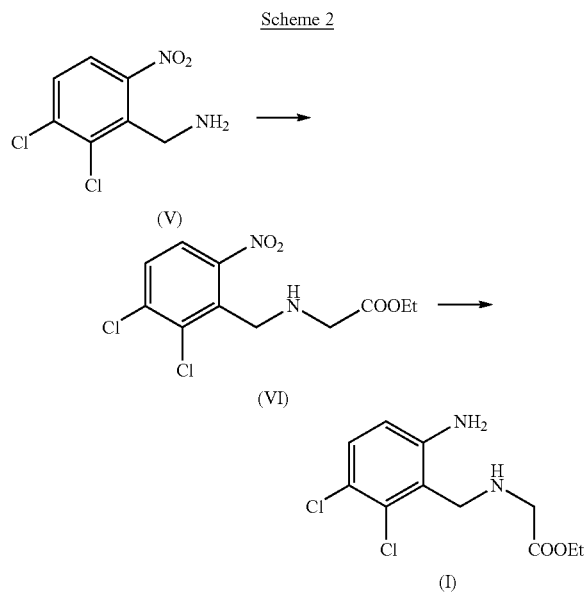

The conventional process for the formation of ethyl-N-(6-amino-2,3-dichlorobenzyl)glycine (compound I) from 1,2,3-trichlorobenzene is shown in U.S. Pat. No. 4,146,718.

An improved process for the formation of ethyl-N-(6-amino-2,3-dichlorobenzyl)glycine (compound I) using the intermediate 2,3-dichloro-6-nitrobenzyl halide (compound VIII), where halide is iodide, chloride or bromide, has been developed as an environmentally acceptable alternative (Scheme 3). The route of preparation from 2,3-dichloro-6-nitro-toluene (compound VII) is described in U.S. Pat. No. 5,801,245, and involves a radical halogenation of the toluene group. Radical conditions can be nonselective, however, and could be difficult to effectively implement in large-scale commercial manufacture.

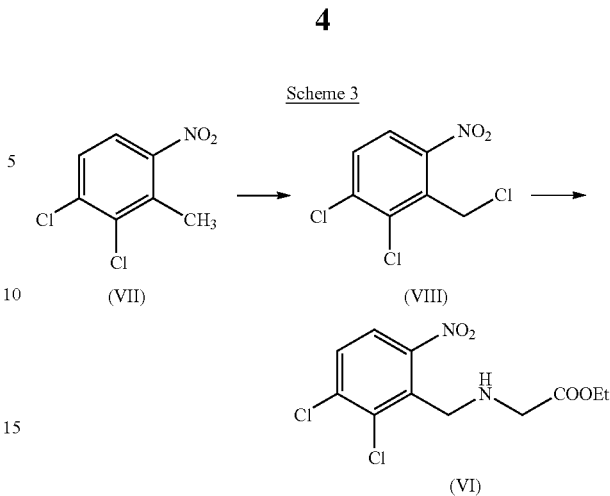

In both of the reactions shown in Schemes 2 and 3, ethyl-N-(2,3-dichloro-6-nitrobenzyl)glycine (compound VI) is reduced to the 8-amino-2,3-dichlorobenzyl glycine (compound I) by stannous chloride reduction ($SnCl_2$/HCl), A disadvantage of this route is the formation of large amounts of tin-containing waste products. In addition, the strongly acidic reaction conditions can promote chlorination of the aromatic ring, producing a mixture of tri-chloro impurities which are difficult to remove in successive steps.

A further problem with these prior art process is the number of synthetic steps required to produce the quinazoline compounds, with each synthetic step leading both to a reduction in yield and increasing the possibility of competing side reactions. Thus, these conventional synthetic routes require effort to purify the intermediate and final products and may not give an optimal yield. Work up and purification may thus be needed after one or more of the intervening steps and final purification is always required.

WO 2010/070318 describes an improved process for making anagrelide and various analogues thereof. In particular, WO 2010/070318 describes a process for making 3,3-dimethylanagrelide by the process shown in Scheme 4 below.

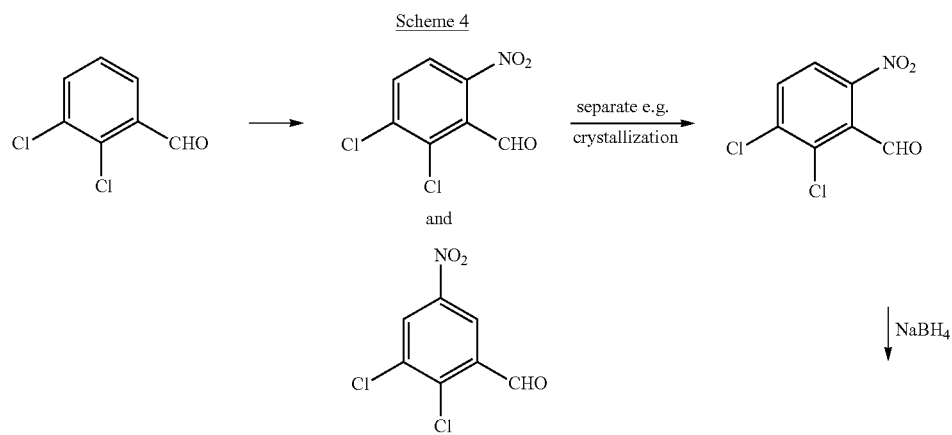

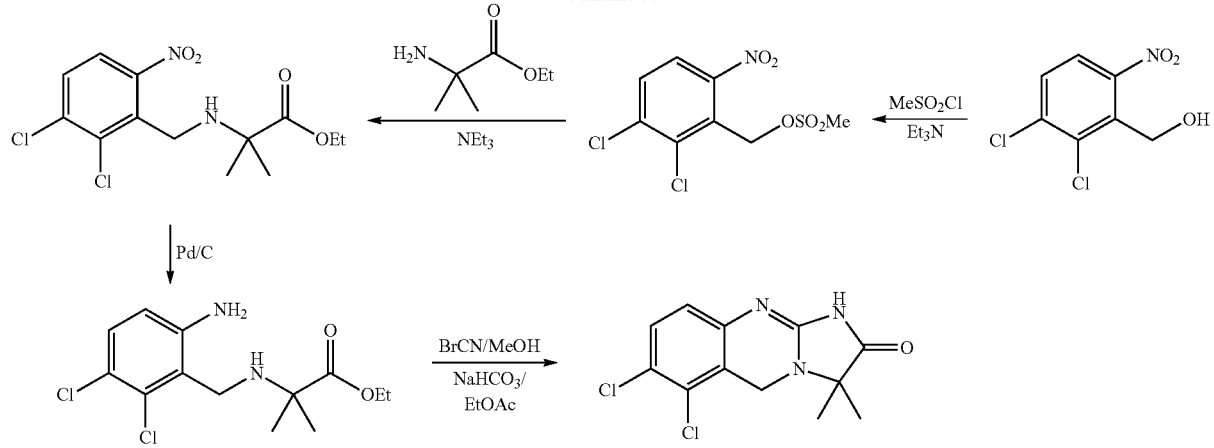

The process described in WO 2010/070318 possesses a number of advantages over the previously described processes. One particular benefit of the process described in WO 2010/070318 is that the 1,1-dimethyl-ethyl N-(2,3-dichloro-6-nitrobenzyl)glycine intermediate and its 1-unsubstituted or substituted analogues can be formed directly from the corresponding 2,3-dichloro-6-nitrobenzyl alcohol without the need to form an intermediate halo derivative. This leads to a number of processing advantages; particularly on a larger scale. It will be appreciated from Scheme 4 above that WO 2010/070318 describes a three step process to get from the 2,3-dichloro-6-nitrobenzaldehyde intermediate to the 1,1-dimethyl-ethyl N-(2,3-dichloro-6-nitrobenzyl)glycine intermediate.

Despite the improvements offered by the process described in WO 2010/070318, there still remains a need for further improved processes for manufacturing anagrelide or analogues thereof, such as 3,3-dimethylanagrelide, which are efficient and commercially viable to implement on a commercial scale.

It is therefore an object of the present invention to provide an improved synthetic process for the making of anagrelide and its analogues, whether in base or salt form.

It is also an aim of the present invention to provide a synthetically efficient process for the production of anagrelide with a reduced number of synthetic steps and which avoids some or all of the drawbacks associated with the prior art processes. It is also an aim to provide a process in which the convergency (i.e. the bringing together of synthetic fragments) is maximised. It is a further aim to ensure that the need for purification and workup is minimised. It is a particular aim of the present invention to provide a process which minimizes the need for intermediate and final purification steps. It is thus an aim to provide a route to the compounds of formula (I) which offers an improved yield relative to the existing routes. It is a further aim of the process of the present invention to avoid the use of expensive and potentially hazardous reagents and to additionally minimise the complexity and costs associated with the process steps wherever possible.

It is an additional aim of the present invention to make suitable intermediates from readily available starting materials. Ideally this is achieved by an environmentally acceptable method.

Still further objects and advantages of the present invention will become apparent from the details provided in the specification.

SUMMARY OF THE INVENTION

According to a first aspect of the present invention there is provided a method for making a compound of formula (A), or a salt thereof:

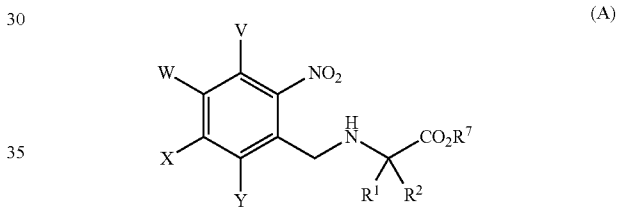

(A)

wherein:

$R^1$ and $R^2$ are each independently hydrogen or a blocking group which functions to directly or indirectly prevent metabolic reaction at the 3-position of substitution;

V, W, X, and Y, are independently chosen from the group comprising: H, F, Cl, I, Br, CN, $C_{1-6}$ alkyl, $C_{1-6}$ haloalkyl, $C_{1-6}$ alkoxy, haloalkoxy and $C_{1-6}$ alkanoyl; and $R^7$ is a $C_{1-6}$ alkyl group or aryl group, each of which can be optionally substituted by 1 to 3 substituents independently selected from the group comprising: $C_{1-6}$alkyl, —$SR^8$, —$OR^9$, —$NR^8R^9$, —$NO_2$, $SCF_3$, halogen, —$C(O)R^8$, —CN, and —$CF_3$, where $R^8$ and $R^9$ are independently H or $C_{1-6}$ alkyl the process comprising the steps of:

(a) reacting a compound of the formula (X):

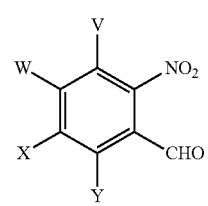

with a glycine derivative of the formula (XI)

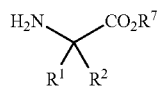

wherein $R^1$, $R^2$ and $R^7$ are as defined above;
in the presence of a suitable base and a suitable solvent to form an imine compound of the formula (XII)

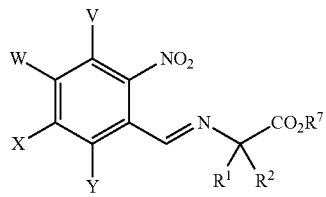

(b) reducing the imine compound of formula (XII) with a suitable reducing agent to form the compound of formula A; and (c) optionally isolating the compound of formula A in the form of an acid addition salt by reacting the compound of formula A with a suitable acid.

As indicated above, compounds of formula A are useful as intermediates in the synthesis of anagrelide and certain analogues thereof, and in particular compounds of formula (B) described below.

The process indicated above possesses a number of advantages relative to the prior art processes. In particular, with regard to the three step process defined in WO 2010/070318 for getting from the 2,3-dichloro-5-nitrobenzaldehyde intermediate to the 1,1-dimethyl-ethyl N-(2,3-dichloro-6-nitrobenzyl)glycine intermediate, the process defined above requires only two key synthetic steps (steps (a) and (b) above). The process defined above has also surprisingly been found to provide an increased yield of the compound of formula A with comparable levels of purity. Furthermore, the batch cycle time can be reduced using this new process and the need to use the potentially hazardous and expensive reagent methanesulphonyl chloride, or related sulphonyl chloride derivatives, is also eliminated. The process of the present invention provides a further cost saving by enabling the use of cheaper solvents, such as, for example, toluene.

In a second aspect, the present invention provides a process for the preparation of a compound of formula (B), or a pharmaceutically acceptable salt thereof:

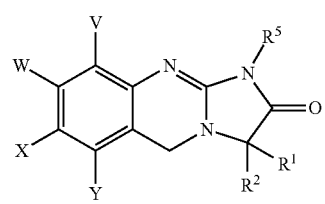

wherein:
$R^1$, $R^2$, V, W, X, and Y are all as defined above in relation to formula A; and
$R^5$ is H, $C_{1-6}$ alkyl or OH;
the process comprising the steps of:

(a) forming a compound of formula A from a compound of formula (X) as defined above;
(b) reducing the compound of formula (A) to form a compound of formula (XIII):

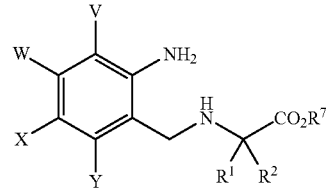

(c) reacting the compound of formula (XIII) prepared in step (b) above with cyanogen bromide in a suitable solvent to form a compound of the formula (XIV)

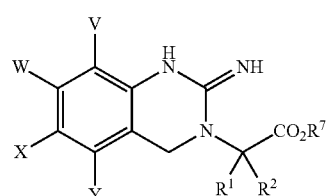

(d) reacting the compound of formula (XIV) under cycloalkylation conditions to form the compound of formula (B); and
(e) optionally thereafter forming a pharmaceutically acceptable salt of the compound of formula (B).

DETAILED DESCRIPTION OF THE INVENTION

Definitions

Unless otherwise stated, the following terms used in the specification and claims have the following meanings:

"Halo" means a group selected from: fluoro, chloro, bromo or iodo.

"Alkyl" as used herein to a straight or branched hydrocarbon chain containing the specified number of carbon atoms. For example, $C_{1-6}$alkyl means a straight or branched alkyl containing at least 1 and at most 6 carbon atoms. Examples of the term "alkyl" as used herein include, but are not limited to, methyl, ethyl, n-propyl, n-butyl, n-pentyl, isobutyl, isopropyl, t-butyl, and hexyl. A $C_{1-4}$ alkyl group is one embodiment, for example methyl, ethyl, n-propyl, isopropyl, n-butyl, isobutyl or t-butyl. The same principle applies to alkyl moieties of other substiuent groups such as, for example, the alkyl moieties of an alkoxy or alkanoyl group.

"Haloalkyl" refers to an alkyl group as defined above which is substituted with one or more halo atoms. Examples of the term haloalkyl include —$CF_3$, —$CHF_2$, —$CH_2CF_3$, —$CHCl_2$, and —$CH_2CHCl_2$. In an embodiment, the halo atoms are selected from fluoro or chloro.

"Haloalkoxy" likewise refers to an alkoxy group that has been substituted with one or more halo atoms. Examples of the term haloalkoxy include —O—$CF_3$ and —O—$CH_2CHCl_2$. In an embodiment, the halo atoms are selected from fluoro or chloro.

The term "aryl" is used herein to refer to phenyl or naphthyl, preferably phenyl.

The following are embodiments of the invention which are relevant to each of the first and second aspects of the invention.

In an embodiment, Y is halo. In a particular embodiment, is chloro.

In an embodiment, X is halo. In a particular embodiment, X is chloro.

In an embodiment, V is H.

In an embodiment, W is H.

In an embodiment, $R^1$ is H or an optionally substituted $C_{1-4}$ alkyl or $C_{3-8}$ cycloalkyl group.

In an embodiment, $R^2$ is H or an optionally substituted $C_{1-4}$ alkyl group or $C_{3-8}$ cycloalkyl.

In an embodiment, $R^1$ and $R^2$ are both methyl or together form a cyclopropyl group.

In a particular embodiment, $R^1$ and $R^2$ are both methyl.

In each of the above embodiments for $R^1$ and $R^2$, one or more hydrogen atoms may be replaced by deuterium. Similarly, one or more carbon atoms may be replaced by $^{13}C$.

In an embodiment, $R^5$ is hydrogen or deuterium. In a particular embodiment, $R^5$ is hydrogen. In an embodiment, $R^7$ is an optionally substituted $C_{1-6}$ alkyl group, and more preferably it is methyl or ethyl.

In a particular embodiment, the compound of formula (B) is anagrelide or 3,3-dimethylanagrelide, i.e. X and Y are chloro; V and W are hydrogen, $R^1$ and $R^2$ are both hydrogen or methyl; and $R^5$ is hydrogen.

In a particular embodiment, the compound of formula (A) is a methyl or ethyl ester of N-(2,3-dichloro-6-nitrobenzyl)glycine or 1,1-dimethyl-N-(2,3-dichloro-6-nitrobenzyl)glycine, i.e. X and Y are chloro; V and W are hydrogen, $R^1$ and $R^2$ are both hydrogen or methyl; and $R^7$ is methyl or ethyl.

Preparation of Compounds of Formula A

As indicated above, the present invention provides a method for making a compound of formula (A) as defined herein, the process comprising the steps of:

(a) reacting a compound of the formula (X):

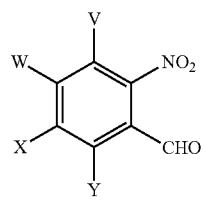

with a glycine derivative of the formula (XI)

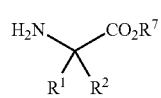

wherein $R^1$, $R^2$ and $R^7$ are as defined above;

in the presence of a suitable base and a suitable solvent to form an imine compound of the formula (XII)

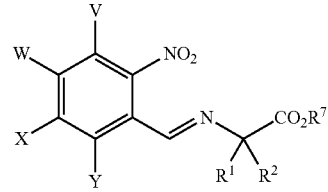

(b) reducing the imine compound of formula (XII) with a suitable reducing agent to form the compound of formula A; and (c) optionally isolating the compound of formula A in the form of an acid addition salt by reacting the compound of formula A with a suitable acid.

The compounds of formula X may be prepared by any suitable process known in the art. For example, methods of making a compound of formula X are described in WO 2010/070318, the entire contents of which are incorporated herein by reference.

Suitably, the compounds of formula (X) are prepared by nitrating a compound of the formula (IX) shown below:

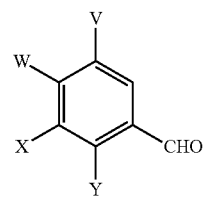

For compounds in which V and W are both hydrogen and X and Y are both chloro, the 2,3-dichlorobenzaldehyde (formula IX) starting material is nitrated preferentially at the 8-position to form 2,3-dichloro-6-nitrobenzaldehyde (formula X). The 2,3-dichloro-6-nitrobenzaldehyde compound can be easily separated by crystallisation as well as by chromatography.

To enable the nitration of the compound of formula (IX), the nitrating agent utilised is suitably nitric acid in concentrated sulphuric acid. In an embodiment, the nitrating agent is fuming nitric acid in concentrated sulfuric acid. In an alternative embodiment, lower strength nitric acid in concentrated sulphuric acid may be used, such as, for example, 60 to 80% nitric acid or, more preferably, 70% nitric acid. The use of lower strength nitric acid is less hazardous. The nitration reaction is conducted for a period of time of from 30 minutes to 5 hours. The reaction may be performed in two stages in the sense that the compound (IX) is first mixed with a solution of sulphuric acid followed by stirring for a period of from 30 minutes to 3 hours and preferably of from 1 to 2 hours. The temperature is maintained at a range of 10 to 50° C. and more preferably of 40 to 45° C. The second stage of this process then involves charging the concentrated nitric acid to the solution of the compound (IX) and sulphuric acid. The resulting reaction mixture is then stirred for a period of from 30 minutes to 3 hours and preferably of from 1 to 2 hours. The temperature is maintained at a range of 10 to 50° C. and more preferably of 20 to 30° C. The reaction mixture is then quenched.

In another embodiment, the compound of formula (IX) may be charged to the nitrating mixture in a single step under the same or similar conditions of temperature i.e. in the range of 10 to 50° C., and stirred for a period of from 30 minutes to 5 hours before quenching.

The nitration reaction is suitably quenched by adding water to form the crude compound of formula (X) as a precipitate. Alternatively, the nitration reaction is quenched by adding the reaction mixture to water to form the compound of formula (X). The reaction is quenched at a temperature of between −10 and 40° C. In some embodiments, the quenching reaction is performed towards the lower end of this range, for example 0 to 5° C.; in other embodiments, the quenching may be performed at a higher temperature such as 15-25° C. The quenching may take place immediately in the sense that water and the reaction mixture are combined immediately or may take place over an extended period such as up to 3 or 4 hours. The resultant crude compound of formula (X) can then be purified, for example by washing and recrystallisation of the crude product or may be used in the next step without further purification.

The glycine derivatives of formula (XI) can be sourced commercially or synthesised using techniques well known in the art.

The reaction of step (a) between the compounds of formulae X and XI is carried out in the presence of a suitable base. The base is preferably an organic base and more preferably is an aliphatic or aromatic amine. In a particular embodiment, the base is a tertiary aliphatic amine.

In a further embodiment, the base is a tri($C_{1-10}$alkyl)amine. In a specific embodiment, the base is triethylamine.

The reaction between the compound of formula X and the glycine derivative of formula (XI) is performed by dissolving the compound of formula X in a suitable solvent, such as toluene, and then adding the resulting solution to a solution of the glycine derivative of formula (XI). Ideally the solution of the glycine derivative is in the same solvent as the compound of formula (X). The base is then added to the resulting mixture and the reaction stirred for a period of from 1 to 4 hours, preferably with heating in order to bring the reaction to reflux.

Any suitable solvent for the step (a) reaction between the compounds of formulae X and XI may be used. Toluene, 2-methyletrahydrofuran, methanol and methyl tert-butyl ether have been demonstrated to work. In a particular embodiment, the solvent is toluene. Toluene is a preferred solvent because of its low cost. Other suitable solvents include: acetonitrile, chlorobenzene, chloroform, cyclohexane, dichloroethane, dichloromethane, dichlorobenzene, dimethoxyethane, DMA, DMF, dioxane, ethoxyethanol, ethyleneglycol, formamide, hexane, heptane, methoxyethanol, methylbutylketone, methylcyclohexane, N-methylpyrrolidine, nitromethane, pyridine, sulfolane, tetralin, trichloroethene, xylene, anisole, butan-1-ol, butan-2-ol, butylacetate, cumene, DMSO, ethanol, diethylether, diisopropylether, ethyl acetate, isopropyl acetate, isobutylacetate, propyl acetate, methylacetate, 3-methyl-1-butanol, methylethylketone, methyl-iso-butylketone, 2-methyl-1-propanol, 1-pentanol, 1-propanol, 2-propanol, tetrahydrofuran, methylisopropylketone, 1,1-diethoxypropane, 1,1-dimethoxymethane, 2,2-dimethoxypropane, isooctane, and methylisopropylketone. One of the important aspects in the choice of the solvent for the reaction is linked to the ability to hold in solution both of the reactants.

The step (a) reaction between the compounds of formulae X and XI suitably proceeds by heating the reaction mixture to an elevated temperature and preferably to reflux. The reaction may proceed for 1 to 24 hours, more suitably 1 to 4 hours, and most typically 2 to 4 hours.

In an embodiment, water is generated during the step (a) reaction is removed by any suitable technique known in the art. In a particular embodiment, the water is removed azeotropically.

After the reaction has been maintained at elevated temperature (e.g. reflux), the reaction is either allowed to cool or forcibly cooled to a temperature around 30-50° C. Cooling may take place over a period of from 15 minutes to 2 hours. The cooled reaction mixture may then be sampled for purity. The purity of the resulting reaction mixture is such that no more than 2% w/w of the compound of formula (X) remains unreacted.

Once the step (a) reaction is complete, the product may be washed with water or an aqueous wash solution and then dried to provide the imine compound of formula (XII). Drying may be facilitated by heating the washed imine product to reflux and azeotrope drying until no more water is observed in the azeotrope collection bowl. The azeotropic drying process may be conducted for a period of from 2 to 4 hours. The dried imine is then cooled and collected. The purity of the dried product of formula XII is such that it contains no more than 1%, and preferably 0.5% w/w water.

The reduction of the imine in step (b) to yield the compound of formula A may be facilitated by any suitable reducing agent. In an embodiment, the reducing agent is a metal hydride. A particularly suitable reducing agent is sodium borohydride.

In an embodiment, the reduction is facilitated by reacting sodium borohydride with acetic acid to form sodium triacetoxyborohydride as the active reducing agent species. The sodium triacetoxyborohydride species can be formed in situ or alternatively it may be preformed and added to the imine of formula (XII).

In an embodiment, sodium borohydride is mixed with acetic acid prior to reaction with the imine compound of formula (XII). The reaction between sodium borohydride and the acetic acid is exothermic, so the reaction vessel is suitably cooled to below 15° C. More suitably, the reaction is maintained at a temperature of between 0 and 10° C.

In an alternate embodiment, sodium borohydride is first added to a reaction vessel and dissolved in a solvent (e.g. toluene) before the imine of formula (XII) is added. The temperature of the reaction vessel may be maintained at a temperature of between 15 and 25° C. After addition of the imine of formula (XII), acetic acid is then added over a period of time of up to 2 hours. During the addition of the acetic acid, the reaction vessel may be maintained at a temperature of between 15 and 25° C. In this embodiment the sodium triacetoxyborohydride species is generated in situ.

When the sodium triacetoxyborohydride species is preformed, the reduction reaction of step (b) is suitably conducted at a temperature between 10 and 40° C., more preferably between 20 and 30° C. for 1 to 24 hours, and more preferably between 6 and 12 hours (for example between 10 and 12 hours).

When the sodium triacetoxyborohydride species is generated in situ the reduction of step (b) is suitably conducted at a temperature of between 10 and 40° C., more preferably between 15 and 25° C. for 1 to 5 hours, and more preferably between 1 and 3 hours.

Suitable solvents for step (b) are the same as for step (a) above. Suitably, the solvent for step (b) is the same as the solvent used for step (a). In an embodiment, toluene is used as the solvent in both of steps (a) and (b).

The purity of the resulting product of formula (A) is such that no more than 4%, and preferably 2%, w/w of the compound of formula (XII) remains unreacted.

The product of step (b) is suitably washed to remove any impurities and then the product is collected, for example by distillation. In an embodiment, the product of step (b) is washed with bicarbonate solution (e.g. 15% w/w sodium bicarbonate solution) and then water and the product is collected by, for example, distillation.

Suitably, the compound of formula A is then reacted to form an acid addition salt that can be collected (as stipulated in step (c) above). Any suitable acid may be used for this purpose. In an embodiment, the acid is hydrochloric acid which yields the HCl salt of the compound of formula (A). The hydrochloride salt is convenient because it facilitates work up and purification where needed after this reaction. In alternative embodiments, HBr or sulfonic acids, eg methanesulfonic acid, are used.

Step (c) is suitably carried out in the presence of a suitable solvent. Any suitable solvent may be used for this process. An example of a suitable solvent is an alcohol, e.g. isopropyl alcohol.

As before, the choice of solvent will depend on solubilities of the reactants; in this case the solubility of free base in the solvent is necessary to ensure the salt formation process works.

Preparation of Compounds of Formula B

As indicated above, the present invention also provides a process for the preparation of a compound of formula (B), or a pharmaceutically acceptable salt thereof:

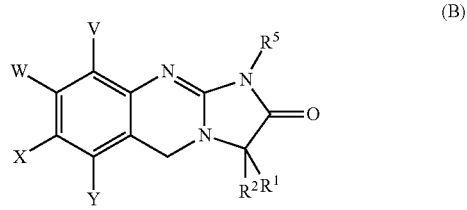

(B)

wherein;
$R^1$, $R^2$, V, W, X, and Y are all as defined above in relation to formula A; and
$R^5$ is H, alkyl or OH;
the process comprising the steps of:
(a) forming a compound of formula A from a compound of formula (X) as defined above;
(b) reducing the compound of formula (A) to form a compound of formula (XIII):

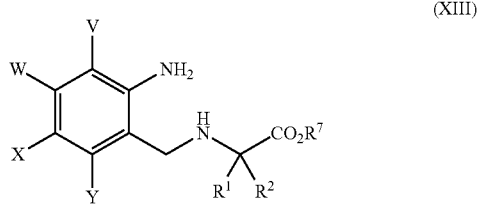

(XIII)

(c) reacting the compound of formula (XIII) prepared in step (b) above with cyanogen bromide in a suitable solvent to form a compound of the formula (XIV)

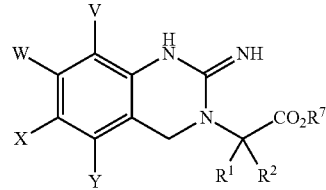

(XIV)

(d) reacting the compound of formula (XIV) under cycloalkylation conditions to form the compound of formula (B); and
(e) optionally thereafter forming a pharmaceutically acceptable salt of the compound of formula (B).

In step (b) of the process defined above, the aromatic nitro group on the glycine derivative of formula (A) is reduced using a conventional reducing agent. One such procedure known in the art is the use of a mixture of stannous chloride and hydrochloric acid to effect the reduction. Where possible, however, the present invention seeks to avoid the use of tin reagents. Preferred catalysts are based on metals or metal complexes of rhodium, iridium, palladium, platinum, ruthenium and osmium. In a preferred embodiment, the compounds of formula (A) are subjected to catalytic hydrogenation using a metal or metal-based catalyst such as platinum, platinum oxide, rhodium, and palladium on carbon under hydrogen pressure. The catalytic hydrogenation reaction may be carried out under homogeneous or heterogeneous conditions. Phase transfer catalysis may also be used using conventional phase transfer catalysts. A preferred catalyst is Pd/C, such as palladium on activated carbon. Once the reaction is complete, the catalyst may be removed by filtration.

In a particular embodiment, the compound of formula (A) is reacted with hydrogen in the presence of a platinum on carbon catalyst until the reaction is complete. In an embodiment, the hydrogenation step is carried out by starting at approximately atmospheric pressure of hydrogen until the rate of hydrogen uptake tails off, followed by gradually increasing the hydrogen pressure as appropriate. The hydrogen gas pressure may be from 1 to 3 bar, and is preferably 2 bar. The hydrogenation reaction is suitably carried out whilst maintaining a temperature of 15-25° C.

In an alternative embodiment, the hydrogenation step is carried out by pressurising the reaction vessel with hydrogen gas. Suitably the reaction proceeds for 2 to 8 hours, for example 6 hours, or until the uptake of hydrogen ceases. Suitably the pressure of the hydrogen gas in the reaction vessel is 1 to 3 bar, especially 2 bar.

Any suitable solvent may be used for the hydrogenation procedure. In an embodiment, the solvent is a water miscible solvent such as methanol. In one embodiment, the compound of formula (A) is added to a vessel containing methanol and the catalyst. Hydrogen is then introduced into the reaction mixture as detailed above.

Suitable conditions for steps (c) and (d) in the process above are known in the art, see for example WO 2010/070318, the entire contents of which are hereby incorporated by reference. For the avoidance of doubt, the content of this disclosure insofar as it relates to steps (c) and (d) forms a part of one embodiment of the process of the present disclosure.

In an embodiment, once the reaction in step (b) is complete and the hydrogenation catalyst has been removed, cyanogen bromide is then added and reacts with the compound of formula (XIII) to form the compound of the formula (XIV). This step (c) reaction is suitably carried out in methanol, although any other suitable water miscible solvents or solvent mixtures may also be used.

Suitably, the reaction between cyanogen bromide and the compound of formula (XIII) is facilitated by heating the reaction mixture to reflux (approximately 65° C. if the solvent is methanol). The reaction may proceed until complete. Reaction times of 2 to 12 hours, more typically 8 to 10 hours may be required. Once the reaction is complete, the reaction mixture is cooled.

The next step in the process, step (d), involves reacting the compound of formula (XIV) formed in step (c) under cycloalkylation conditions. Suitably, the cycloalkylation of the compound of formula (XIV) is facilitated by refluxing the compound in an organic alcohol in the presence of a suitable base. Any suitable base may be used. In an embodiment the base is sodium bicarbonate. In alternative embodiment, the base is sodium carbonate. The carbonate or bicarbonate may be added as an aqueous solution to the reaction mixture. Preferably, the base added to quench the reaction is sodium carbonate as this requires a much lower volume of solution to be added, which dramatically reduces the volume that needs to be filtered in order to collect the final product. This in turn reduces the filtering time dramatically, resulting in significant savings in terms of time and cost.

In an embodiment, a 15% w/w sodium carbonate solution is added and the reaction mixture is maintained at a temperature of 30 to 50° C., more preferably 35 to 45° C., for a time period of 2 to 7 hours, more preferably 3 to 5 hours. The temperature may then be reduced (for example to 20 to 25° C.). The cooled reaction mixture may continue to be stirred for at least one hour.

The resultant compound of formula (B) prepared by the reaction described in step (d) may then be collected by filtration and washed (optionally with water and/or acetone) and then dried.

In step (e), the free base of the compound of formula (B) may optionally be converted into a pharmaceutically acceptable acid addition salt by dissolving the free base in a suitable solvent and adding the appropriate acid. The salt may then be collected by any suitable technique known in the art. It is not necessary for the free base of the compound of formula (B) to be isolated prior to salt formation. The desired salt can be generated by adding the appropriate acid to the crude free base prepared in step (d). The desired salt can then be collected, washed and dried in a similar manner.

The present invention includes the synthesis of all pharmaceutically acceptable isotopically-labelled compounds of formulae (A), (B) and (IX) to (XIV) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, ($^2$H and $^3$H), carbon, ($^{11}$C, $^{13}$C and $^{14}$C), chlorine, ($^{36}$Cl), fluorine, ($^{13}$F), iodine, ($^{123}$I and $^{125}$I), nitrogen, ($^{13}$N and $^{15}$N), oxygen, ($^{15}$O, $^{17}$O and $^{18}$O), phosphorus, ($^{32}$P), and sulphur, ($^{35}$S).

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$O, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{18}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

The skilled person will appreciate that adaptation of the methods herein described and/or adaptation of methods known in the art could be applied to the processes of the present invention.

For example, the skilled person will be immediately familiar with standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (6th edition (2007) or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

EXAMPLES 1A. 2,3-Dichloro-6-nitrobenzaldehyde

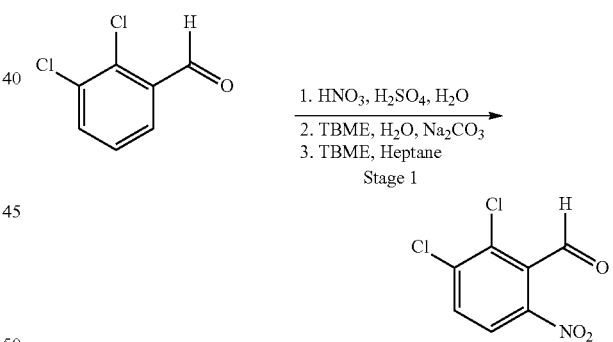

Preparation of 2,3-Dichloro-6-nitrobenzaldehyde

Concentrated sulphuric acid (450 Kg) was added to 2,3-dichlorobenzaldehyde (59 Kg) and the mixture was heated to 40-44° C. for 2 hours, with stirring, to dissolve all the solids then cooled to 20-25° C. over a period of 95 minutes. Nitric acid (70% w/w, 34.5 Kg) was added to the solution, maintaining the temperature between 16 and 28° C., over a period of 110 minutes. The reaction mixture was stirred for 130 minutes, at between 21-25° C., and then quenched by controlled addition over 225 minutes into 1080 Kg of water (pre-cooled to 0-5° C.), maintaining the temperature between 2-20° C., including a vessel rinse of concentrated sulphuric acid (9.2 Kg). The resulting suspension was stirred for 180 minutes at between 10-14° C. then isolated by filtration and washed with pre-cooled (0-15° C.) water (2×297 Kg). The isolated crude solid (151.3 Kg crude, 51.6 kg active weight) was dissolved in methyl tert-butyl ether (590 L) and washed with water (165 L), 10% w/w sodium carbonate solution (165 L) and then water (165 4 Solvent was removed by reduced pressure distillation at 17-20° C. until a volume of 160 L was reached, whereupon heptane (1140 L) was added. The resulting slurry was heated to 60° C. over 54 minutes and stirred at between 60-65° C. for 110 minutes, then cooled to 15-20° C. over 11.5 hours. Material was isolated by filtration and washed with heptane 90 L) then dried in vacuo at 40-45° C. to give 2,3-dichloro-6-nitrobenzaldehyde (21.3 Kg) with 96.3% purity (HPLC) in 29% yield.

$^1$H NMR (CDCl$_3$, 400 MHz): δ 10.4 (a, 1H); δ 8.0 (d, 1H); δ 7.8 (d, 1H)

2A. 2-aminoisobutyric acid ethyl ester hydrochloride

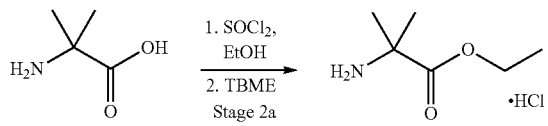

Ethanol (395 L) was added to 2-aminoisobutyric acid (79 Kg) and the mixture stirred at 20° C. Thionyl chloride (91.2 Kg) was added, maintaining the temperature at 540° C. The mixture was heated to reflux and stirred for 6 hours. The contents were distilled under atmospheric pressure to a residual volume of approximately 200 L over a period of 14 hours. The mixture was cooled to 45-50° C. and methyl tert-butyl ether (395 L) was added. The mixture was cooled to 0-5° C. and stirred for 1 hour. Material was isolated by filtration and washed with methyl tert-butyl ether (160 L) pre-cooled to 0-5° C., then dried in vacuo at 30-40° C. to give ethyl-2-aminoisobutyrate hydrochloride (105.5 Kg) with 86.2% purity in 71% yield (based on active).

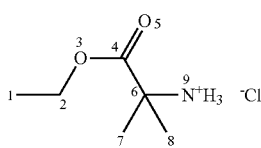

| Chemical Shift (ppm) | Signal, H's | Tentative Assignment |
| --- | --- | --- |
| 1.2 | D, 3H | 1 |
| 1.5 | D, 6H | 7, 8 |
| 2.5 | Quintet | DMSO |
| 3.4 | BS | Water |
| 4.2 | Quartet, 2H | 2 |
| 8.8 | BS, 3H* | 9 |

* = The amine has 3 protons rather than 2 because it is protonated in the HCl in the solution.

3A. Ethyl 1-[(2,3-dichloro-6-nitrobenzyl)amino]isobutyrate hydrochloride (via the imine)

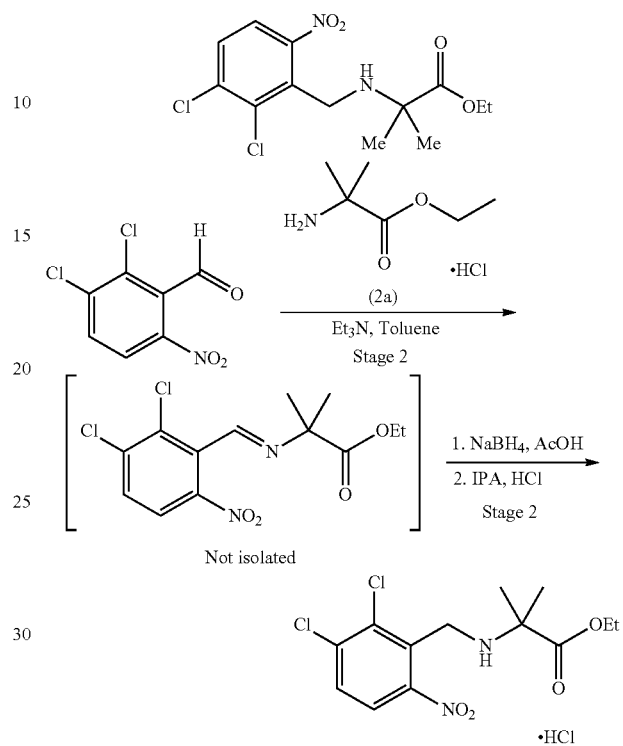

Part A

Ethanol (325 Kg) was charged with 2-Aminoisobutyrate hydrochloride (37.1 Kg) and the mixture stirred at 520° C. Thionyl chloride (13.2 Kg) was added over 10 minutes maintaining temperature at 15-22° C. and the mixture heated to reflux (77° C.) over a period of 93 minutes. The mixture was stirred at reflux for 250 minutes, cooled to 5.40° C., toluene (20 L) was added and the mixture distilled at atmospheric pressure to a residual volume of 100 L over a period of 405 minutes. Toluene (200 L) was added to the residue and the mixture distilled under vacuum to a residual volume of 100 L over a period of 125 minutes maintaining the temperature ≤42° C. Toluene (200 L) was added to the residue and the mixture distilled under vacuum to a residual volume of 100 L over a period of 180 minutes maintaining the temperature ≤44° C.

Part B

Toluene (250 L) was added to 2,3-dichloro-6-nitrobenzaldehyde (46.4 Kg) and the mixture stirred at 20-23 minutes until a solution forms (1 hour). The solution was added to the 2-aminoisobutyrate hydrochloride solution from part A, followed by a line rinse of toluene (50 L) Triethylamine (31.9 Kg) was added to the solution over a period of 25 minutes maintaining the temperature between 17 and 20° C., followed by toluene (10 L). The mixture was heated to 110° C. and stirred under azeotropic reflux for 185 minutes at which point the in-process check indicated <2% 2,3-dichloro-6-nitrobenzaldehyde remaining. The mixture was cooled to 20-25° C. and washed with water (2×225 L) then heated to reflux and stirred under azeotropic reflux for 325 minutes at which point the in-process check indicated a water content of <0.5% w/w, Part C Toluene (270 L) was added to sodium borohydride (16 Kg), the mixture stirred at 0-5°C and acetic acid (102.1 Kg) was added over a period of 190 minutes maintaining the temperature between 0 and 20° C., followed by toluene (10 L). The imine solution from Part B was added to the mixture over a period of 95 minutes maintaining the temperature between 1-8° C., followed by toluene (SOL then 200. The mixture was warmed to 20-30° C. and stirred at 22-28° C. for 12 hours at which point the in-process check indicated 54% imine remaining, 15% Sodium carbonate solution (370 L) was added to the mixture maintaining the temperature between 20-30° C., the mixture stirred for 105 minutes and the layers separated. The organic layer was washed with water (225 L), the organic solution concentrated in-vacuo at 18-30° C. to minimum stir volume, isopropyl alcohol (675 L) added and the solution concentrated in-vacuo at 18-29° C. to minimum stir volume. A solution of HCl in isopropyl alcohol (15.7% w/w HCl, 73.6 Kg) was added to the imine solution maintaining the temperature between 15-21° C. over a period of 22 minutes, the mixture cooled to 0-5° C. over 35 minutes, stirred at 2-5° C. for 135 minutes and then filtered, washed with isopropyl alcohol (2×100 L, pre-cooled to 0-5° C.) and dried on the filter, until the loss on drying indicates ≤20% w/w, to give ethyl 1-[(2,3-dichloro-6-nitrobenzyl)amino]isobutyrate hydrochloride (61.8 Kg, active yield 57.2 Kg) with 92.68% purity, by HPLC, in 75% yield.

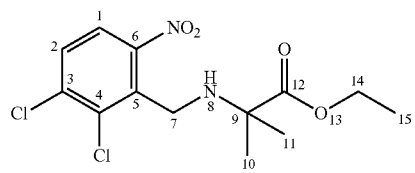 [SMILES: CCOC(=O)C(C)(C)NCc1c([N+](=O)[O-])ccc(Cl)c1Cl]

| Chemical Shift (ppm) | Signal, H's | Tentative Assignment |
| --- | --- | --- |
| 1.26 | T, 3H | 15 |
| 1.66 | BS, 6H | 10, 11 |
| 4.26 | Q, 2H | 14 |
| 4.76 | BS, 2H | 7 |
| 8.07 | D, 1H | 2 |
| 8.24 | D, 1H | 1 |
| 9.88 | BS, H | 8 |

4A. 3,3-Dimethylanagrelide

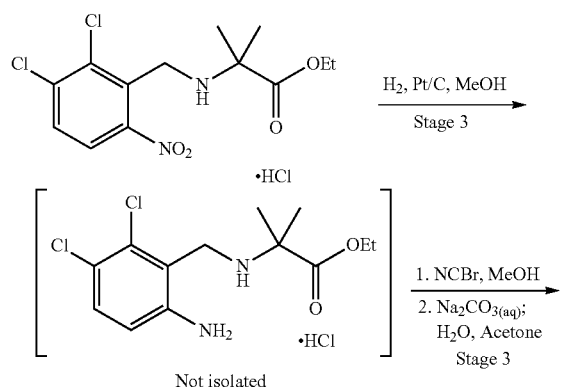

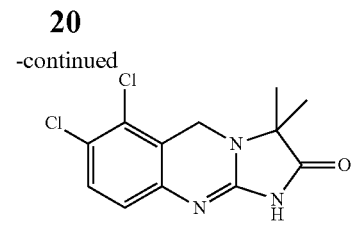

Methanol (151 Kg) was added to 5% platinum on activated carbon (1.78 Kg) and ethyl 1-[(2,3-dichloro-6-nitrobenzyl)amino]isobutyrate hydrochloride (17.81 Kg) added, followed by methanol (40 Kg). The mixture was stirred under hydrogen (2 bar) for 7 hours at between 20-27° C. after which period the in-process check indicated reaction completion. The reaction mixture was purged under nitrogen, filtered and the filter cake washed with methanol (47.5 Kg). Cyanogen bromide (7.6 Kg) was added to the methanol solution of ethyl 1-[(6-amino-2,3-dichlorobenzyl)amino]isobutyrate hydrochloride at 20-25° C., followed by methanol (10 L) and the mixture heated to, and stirred at 63-64° C. for 10 hours at which point the in-process check indicated 1.7% ethyl 1-[(6-amino-2,3-dichlorobenzyl)amino]isobutyrate remaining. The mixture was cooled to 38° C., 15% sodium carbonate solution (43 Kg) added maintaining the temperature between 37-38° C. and the mixture stirred at 38-40° C. for 285 minutes. The mixture was cooled to 20-25° C. over a period of 70 minutes, stirred at 2025° C. for 80 minutes, filtered and the filter cake slurried with water (3×50 L), then acetone (50 L) and the product dried at 45° C. for 8 hours to give 3,3-dimethylanagrelide (8 Kg) with 99.28% w/w purity, by HPLC, in 60% yield 5A. 3,3-Dimethylanagrelide Tosylate

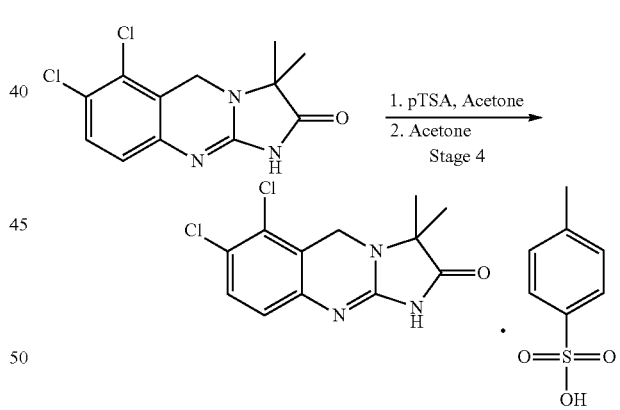

Part A 3,3-Dimethylanagrelide (7.1 Kg) was added to Acetone (232 L), followed by a line rinse of acetone (40 Kg). The slurry was stirred at 20-21° C. for 35 minutes and paratoluene sulphonic acid monohydrate (5.1 Kg), dissolved in acetone (15.4 L), was added followed by a line rinse of acetone (15.4 L). The mixture was heated to reflux (58° C.) over a period of 52 minutes, stirred at reflux for 45 minutes, filtered, the filter washed with acetone (20 L, pre-heated to 40-45° C.) and the mixture concentrated by atmospheric distillation, over a period of 205 minutes, to a residual volume of approximately 90 L. The solution was held at 42-49° C. for 4.5 hours.

Part B 3,3-Dimethylanagrelide (7.1 Kg) was added to Acetone (232 L), followed by a line rinse of acetone (40 Kg). The slurry was stirred at 18-20° C. for 56 minutes and para-toluene sulphonic acid monohydrate (5.1 Kg), dissolved in acetone (15.4 L), added followed by a line rinse of acetone (15.4 L). The mixture was heated to reflux (58° C.) over a period of 25 minutes, stirred at reflux for 35 minutes, filtered, the filter washed with acetone (20 L, pre-heated to 40-45° C.) and the solution added to the solution formed in Part A. The mixture was heated to reflux over a period of 23 minutes and then the mixture concentrated by atmospheric distillation, over a period of 195 minutes, to a residual volume of 225 L. The mixture was stirred at reflux for 20 minutes, cooled to 5° C. over a period of 190 minutes and stirred at 2-5° C. for 1 hour. The mixture was filtered, the filter cake washed with acetone (32 L) pre-cooled to 0-5° C. and the solid dried in-vacuo at 45° C. for 33 hours to give 3,3-dimethy-lanagrelide tosylate (17.5 Kg) with 99.7% purity, by HPLC, in 78% yield.

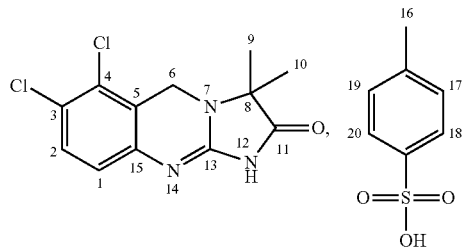

| Chemical Shift (ppm) | Signal, H's | Tentative Assignment |
|---|---|---|
| 7.64 | D, 1H | 2 |
| 7.49 | D, 2H | 17, 19 |
| 7.13 | Q, 3H | 1, 18, 20 |
| 4.68 | S, 2H | 6 |
| 2.28 | S, 3H | 16 |
| 1.47 | S, 6H | 9, 10 |

1B. 2,3-Dichloro-6-nitrobenzaldehyde

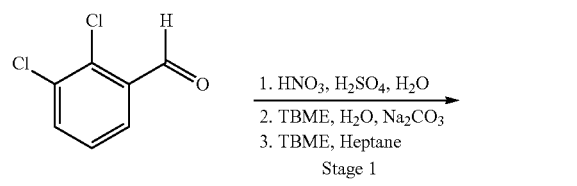

Preparation of 2,3-Dichloro-6-nitrobenzaldehyde

Concentrated sulphuric acid (450 Kg) was added to 2,3-dichlorobenzaldehyde (59 Kg) and the mixture was heated to 40-45° C. for 1 to 2 hours, with stirring, to dissolve all the solids then cooled to 20-25° C. over a period of up to 60 minutes. Nitric acid (70% w/w, 34.5 Kg) was added to the solution, maintaining the temperature between 15 and 30° C., over a period of up to 30 minutes. The reaction mixture was stirred for 1 to 2 hours, at between 20-30° C., and then quenched by controlled addition over a period up to 3 hours into 1080 Kg of water (15-25° C.), maintaining the temperature between 15-25° C., including a vessel rinse of concentrated sulphuric acid (9.2 Kg). The resulting suspension was stirred for a period up to about 30 minutes at between 15-25° C. then isolated by filtration and washed with water (15-25° C., 2×297 g).

The isolated crude solid was dissolved in methyl tert-butyl ether (590 L) and washed with water (165 L), 10% w/w sodium carbonate solution (165 L) and then water (185 L). Solvent was removed by distillation at atmospheric pressure until a volume of 130 L was reached. The vessel was cooled to 35-40° C. whereupon heptane (1140 L) was added. The resulting slurry was heated to 25-30° C. Material was isolated by filtration and washed with heptane (90 L) then dried in vacuo at 40-45° C. to give 2,3-dichloro-6-nitrobenzaldehyde.

$^1$H NMR (CDCl$_3$, 400 MHz): δ 10.4 (s, 1H); δ 8.0 (d, 1H); δ 7.8 (d, 1H)

2B. 2-aminoisobutyric acid ethyl ester hydrochloride

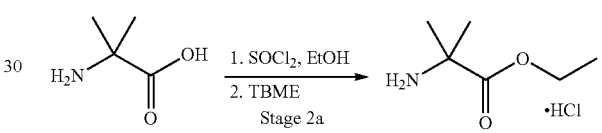

Ethanol (400 L) was added to 2-aminoisobutyric acid (22.0 Kg). Thienyl chloride (30 Kg) was added to the mixture, maintaining the temperature at 5.40° C. The mixture was heated to reflux and stirred for a period of 4 to 6 hours. The reaction mixture was cooled to 5.40° C. The contents were distilled under atmospheric pressure to a residual volume of approximately 100 L.

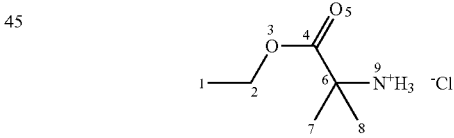

| Chemical Shift (ppm) | Signal, H's | Tentative Assignment |
|---|---|---|
| 1.2 | D, 3H | 1 |
| 1.5 | D, 6H | 7, 8 |
| 2.5 | Quintet | DMSO |
| 3.4 | BS | Water |
| 4.2 | Quartet, 2H | 2 |
| 8.8 | BS, 3H* | 9 |

* = The amine has 3 protons rather than 2 because it is protonated in the HCl in the solution.

3B. Ethyl 1-[(2,3-dichloro-6-nitrobenzyl)amino]isobutyrate hydrochloride (via the imine)

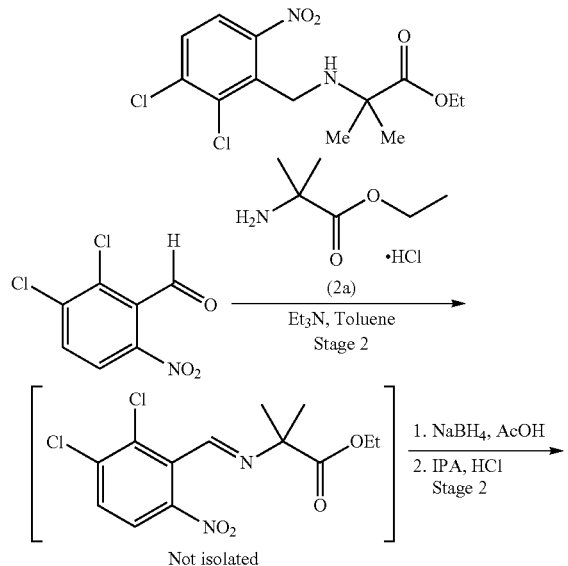

Toluene (250 L) was added to 2,3-dichloro-6-nitrobenzaldehyde (42.0 Kg) and the mixture stirred until a solution forms (30 minutes). The solution was added to the 2-aminoisobutyrate hydrochloride solution from Example 2A above, followed by a line rinse of toluene (50 L). Triethylamine (29 Kg) was added to the solution over a period of up to about 30 minutes, followed by the addition of toluene (10 L). The mixture was heated to reflux and stirred under azeotropic reflux for 3 hours at which point the in-process check indicated <2% 2,3-dichloro-6-nitrobenzaldehyde remaining. The contents were washed with water (2×225 L) then heated to reflux and stirred under azeotropic reflux until no more water was observed in the azeotrope bowl. The contents were cooled to 40° C. at which point the in-process check indicated a water content of <0.5% w/w.

Toluene (150 L) was added to sodium borohydride (7.9 Kg), and the mixture stirred at 15-25° C. The imine solution obtained in the above paragraph was charged to the toluene/sodium borohydride mixture, maintaining the temperature at 15-25° C. A toluene line rinse was carried out (20 L). Acetic acid (52 Kg) was added over a period of up to 120 minutes maintaining the temperature between 15 and 25° C., followed by toluene (10 L) as a line rinse. The mixture was stirred for no longer than 3 hours at which point the in-process check indicated 52% imine remaining.

15% Sodium carbonate solution (250 L) was added to the mixture maintaining the temperature between 15 and 25° C., the mixture stirred for 1 to 2 hours and the layers separated. The organic layer was washed with water (225 L) and the organic solution concentrated in-vacuo at no more than 60° C. to minimum stir volume. A solution of Ha in isopropyl alcohol (15.7% w/w HC) was added to the imine solution maintaining the temperature between 15-25° C., the mixture cooled to −5 to 0° C. and stirred for 1 to 3 hours and then filtered, washed with isopropyl alcohol (2×100 L, pre-cooled to 0-5° C.) and dried on the filter, until the loss on drying indicates ≤5%/w/w, to give, ethyl 1-[(2,3-dichloro-6-nitrobenzyl)amino]isobutyrate hydrochloride.

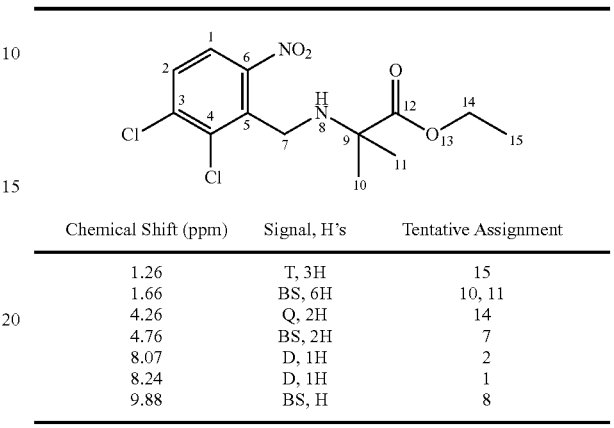

| Chemical Shift (ppm) | Signal, H's | Tentative Assignment |
|---|---|---|
| 1.26 | T, 3H | 15 |
| 1.66 | BS, 6H | 10, 11 |
| 4.26 | Q, 2H | 14 |
| 4.76 | BS, 2H | 7 |
| 8.07 | D, 1H | 2 |
| 8.24 | D, 1H | 1 |
| 9.88 | BS, H | 8 |

4B. 3,3-Dimethylanagrelide

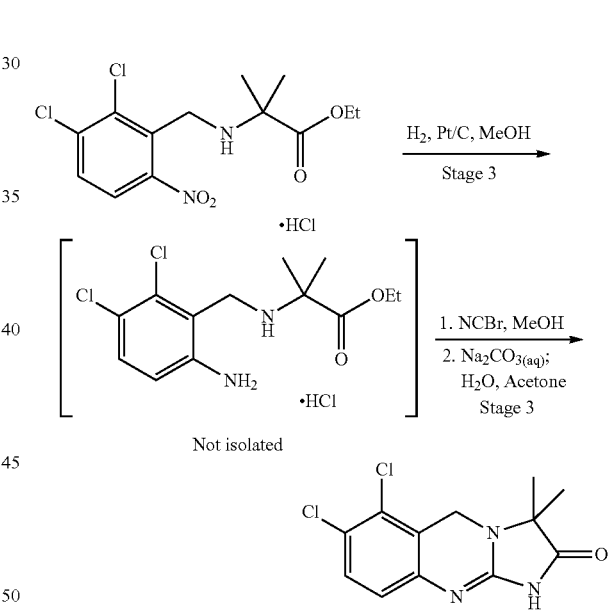

Methanol (570 Kg) was added to 5% platinum on activated carbon (5.3 Kg) and ethyl 1-[(2,3-dichloro-6-nitrobenzyl)amino]isobutyrate hydrochloride (53.0 Kg) added, followed by methanol (40 Kg). Hydrogenation was then carried out by first starting at approximately atmospheric pressure until hydrogen uptake tailed off after which the hydrogen pressure was gradually increased to 2 bar whilst maintaining at 15-20° C. The mixture was stirred at 15-25° C. under hydrogen (2 bar) until hydrogen uptake stops after which period the in-process check indicated reaction completion. The reaction mixture was purged under nitrogen, filtered and the filter cake washed with methanol (80 Kg).

Cyanogen bromide (22.7 Kg) was added to the methanol solution of ethyl 1-[(6-amino-2,3-dichlorobenzyl)amino]isobutyrate hydrochloride at 15-25° C., followed by methanol (50 L) as a line rinse and the mixture heated to, and stirred at, 63-64° C. for 8 to 10 hours at which point the in-process check indicated less than 4% ethyl 1-[(6-amino-2,3-dichlorobenzyl)amino]isobutyrate remaining. The mixture was cooled to 35-45° C., 15% sodium carbonate solution (128 Kg) added maintaining the temperature between 35-45° C. and the mixture stirred at 35-45° C. for 4-6 hours. The mixture was cooled to 20-25° C. and stirred for 60 minutes, filtered and the filter cake slurried with water (300 L), then acetone (200 L) and the product dried for no longer than 12 hours to give 3,3-dimethylanagrelide.

5B. 3,3-Dimethylanagrelide Tosylate

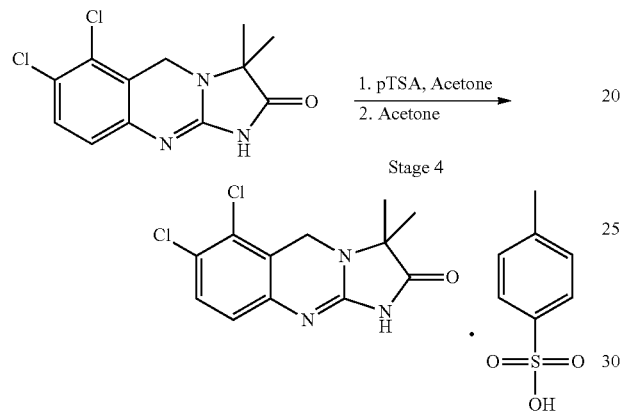

Part A 3,3-Dimethylanagrelide (20 Kg) was added to acetone (800 L), followed by a line rinse of acetone (16 Kg) and the siurry was stirred. Para-toluene suiphonic acid monohydrate (75 Kg) was mixed with acetone (178 Kg) and the mixture stirred for 30 mins. The para-toluene sulphonic acid/acetone solution (50 Kg) was added to the 3,3-Dimethylanagrelide/acetone solution followed by a line rinse of acetone (20 L). The mixture was heated to reflux (56° C.) over a period of up to 30 minutes, filtered, the filter washed with acetone (20 L, pre-heated to 40-45° C.) and the mixture concentrated by atmospheric distillation to a residual volume of approximately 360 L. The solution was held at 35-50° C.

Part B 3,3-Dimethylanagrelide (20 Kg) was added to Acetone (800 L, followed by a line rinse of acetone (16 Kg) and the slurry was stirred. Para-toluene sulphonic acid monohydrate (75 Kg) was mixed with acetone (178 Kg) and the mixture stirred for 30 mins. The para-toluene sulphonic acid/acetone solution (50 Kg) was added to the 3,3-Dimethylanagrelide/acetone solution followed by a line rinse of acetone (20 L). The mixture was heated to reflux (56° C.) over a period of up to 30 minutes, filtered, the filter washed with acetone (20 L, pre-heated to 40-45° C.) and the solution added to the solution formed in Part A. The mixture concentrated by atmospheric distillation to a residual volume of approximately 360 L.

The mixture was heated to reflux over a period of 15-60 minutes. The mixture was then cooled to 0-5° C. ensuring a smooth cooling profile is achieved (a batch temperature drop of approximately 10-15° C. per hour). The mixture was held at 0-5° C. for 30 mins. The mixture was filtered, the filter cake washed with acetone (75 L) pre-cooled to 0-5° C. and the solid dried to give 3,3-dimethylanagrelide tosylate. The tosylate salt is a particularly convenient form of 3,3-dimethyl anagrelide because it is crystalline, soluble and easy to work with enabling further purification to high levels of purity if required.

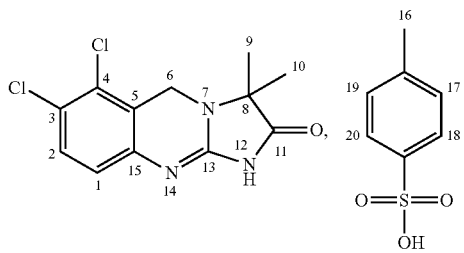

| Chemical Shift (ppm) | Signal, H's | Tentative Assignment |
|---|---|---|
| 7.64 | D, 1H | 2 |
| 7.49 | D, 2H | 17, 19 |
| 7.13 | Q, 3H | 1, 18, 20 |
| 4.68 | S, 2H | 6 |
| 2.28 | S, 3H | 16 |
| 1.47 | S, 6H | 9, 10 |

The invention claimed is:
1. A process for the preparation of a compound of formula (A), or a salt thereof:

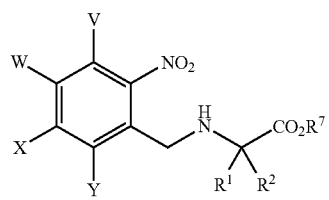

wherein:
$R^1$ and $R^2$ are each independently hydrogen or a blocking group which functions to directly or indirectly prevent metabolic reaction at the 3-position of substitution;
V and W are independently chosen from the group consisting of: H, F, Cl, I, Br, CN, $C_{1-6}$ alkyl, $C_{1-6}$ haloalkyl, $C_{1-6}$ alkoxy, $C_{1-6}$ haloalkoxy and $C_{1-6}$ alkanoyl;
X and Y are independently selected halo's; and
$R^7$ is a $C_{1-6}$ alkyl group or aryl group, each of which can be optionally substituted by 1 to 3 substituents independently selected from the group comprising: $C_{1-6}$ alkyl, $C_{1-6}$ haloalkyl, —$SR^8$, —$OR^9$, —$NR^8R^9$, —$NO_2$, $SCF_3$, halogen, —C(O)$R^8$, —CN, and —$CF_3$, where $R^8$ and $R^9$ are independently H or $C_{1-6}$ alkyl
the process comprising the steps of:
(a) reacting a compound of the formula (X):

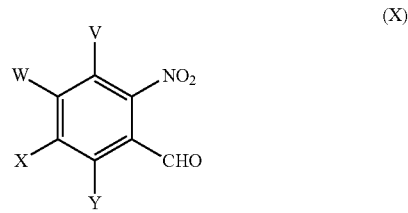

with a glycine derivative of the formula (XI)

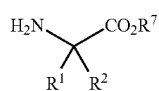

in the presence of a suitable base and a suitable solvent to form an imine compound of the formula (XII)

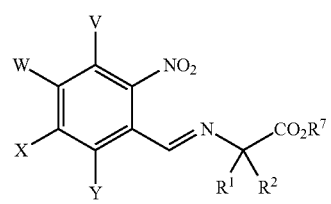

(b) reducing the imine compound of formula (XII) with a suitable reducing agent to form the compound of formula A; and
(c) optionally isolating the compound of formula A in the form of an acid addition salt by reacting the compound of formula A with an suitable acid.

2. A process for the preparation of a compound of formula (B), or a pharmaceutically acceptable salt thereof:

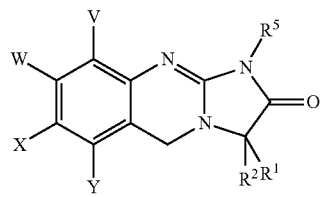

wherein:
$R^1$, $R^2$, V, W, X, and Y are all as defined in claim 1; and
$R^5$ is H, $C_{1-6}$ alkyl or OH;
the process comprising the steps of:
(a) forming a compound of formula A from a compound of formula (X) as defined in claim 1;
(b) reducing the compound of formula (A) to form a compound of formula (XIII):

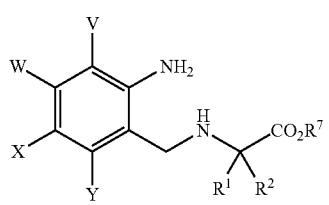

(c) reacting the compound of formula (XIII) prepared in step (b) above with cyanogen bromide in a suitable solvent to form a compound of the formula (XIV)

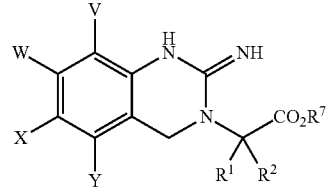

(d) reacting the compound of formula (XIV) under cycloalkylation conditions to form the compound of formula (B); and
(e) optionally thereafter forming a pharmaceutically acceptable salt of the compound of formula (B).

3. The process according to claim 1, wherein X and Y are chloro.

4. The process according to claim 1, wherein W and V are hydrogen.

5. The process according to claim 1, wherein $R^1$ and $R^2$ are both selected from hydrogen or methyl.

6. The process according to claim 1, wherein $R^1$ and $R^2$ are both methyl.

7. The process according to claim 2, wherein $R^5$ is hydrogen.

8. The process according to claim 1, wherein $R^7$ is methyl or ethyl.

9. The process according to claim 2, wherein X and Y are chloro; V and W are hydrogen, $R^1$ and $R^2$ are both methyl; and $R^5$ is hydrogen.

10. The process according to claim 1, wherein X and Y are chloro; V and W are hydrogen, $R^1$ and $R^2$ are both hydrogen or methyl; and $R^7$ is methyl or ethyl.

11. The process according to claim 1, wherein the compounds of formula (X) are prepared by nitrating a compound of the formula (IX) shown below:

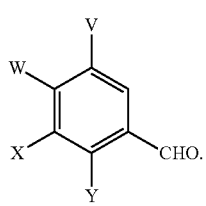

* * * * *